(12) United States Patent
Kleinman et al.

(10) Patent No.: US 7,268,118 B2
(45) Date of Patent: Sep. 11, 2007

(54) THYMOSIN β4 COMPOSITIONS

(75) Inventors: Hynda K. Kleinman, Kensington, MD (US); Allan L. Goldstein, Washington, DC (US); Katherine M. Malinda, Millersville, MD (US); Gabriel Sosne, Oak Park, MI (US)

(73) Assignee: United States of America as represented by The Secretary of Health, Washington, DC (US)

( * ) Notice: Subject to any disclaimer, the term of this patent is extended or adjusted under 35 U.S.C. 154(b) by 0 days.

(21) Appl. No.: 10/853,505

(22) Filed: May 26, 2004

(65) Prior Publication Data

US 2004/0220111 A1 Nov. 4, 2004

Related U.S. Application Data

(63) Continuation of application No. 09/772,445, filed on Jan. 29, 2001, which is a continuation of application No. PCT/US99/17282, filed on Jul. 29, 1999.

(60) Provisional application No. 60/094,690, filed on Jul. 30, 1998.

(51) Int. Cl.
*A61K 38/00* (2006.01)
*A61K 38/24* (2006.01)

(52) U.S. Cl. ............................. 514/17; 514/12; 514/2; 530/399; 930/180

(58) Field of Classification Search ................ 514/183, 514/12, 2, 15; 260/112; 424/177
See application file for complete search history.

(56) References Cited

U.S. PATENT DOCUMENTS

| 4,389,343 A | * | 6/1983 | Horecker | ................... 530/324 |
| 4,543,340 A | | 9/1985 | Goldstein et al. | |
| 5,578,570 A | * | 11/1996 | Goldstein et al. | ............. 514/12 |
| 5,663,071 A | | 9/1997 | Zetter et al. | |
| 6,030,948 A | | 2/2000 | Mann | |
| 6,602,519 B1 | | 8/2003 | Stevenson et al. | |

FOREIGN PATENT DOCUMENTS

| EP | 0 124 779 | | 11/1984 |
| EP | 0 450 240 | A1 | 10/1991 |
| EP | 1 100 529 | B1 | 5/2001 |
| WO | WO94/11499 | | 5/1994 |
| WO | WO94/18988 | A2 | 9/1994 |
| WO | WO94/23739 | A1 | 10/1994 |
| WO | WO95/09646 | A1 | 4/1995 |
| WO | WO96/16983 | | 6/1996 |
| WO | WO97/48805 | | 12/1997 |
| WO | WO99/49883 | A2 | 10/1999 |

OTHER PUBLICATIONS

Malinda et al., FASEB Journal, vol. 11, No. 6, May 1997, pp. 474-481.*
Malinda, K.M., et al., "Thymosin B4 stimulates directional migrational of human umbilical vein endothelial cells," FASEB Journal, vol. 11, No. 6 (1997), pp. 474, 481.
Sun, H-Q, et al., "B-Thymosins are not simple actin monomer buffering proteins. Insights from overexpression studies," Journal of Biological Chemistry, vol. 271, No. 16 (1996), pp. 9223-9230.
Nimni, M.E., "Polypeptide growth factors: targeted delivery systems," BIOMATERIALS, vol. 18, No. 18 (1997), pp. 1201-1225.
Frank, S., et al., "Regulation of vascular endothelial growth factor expression in cultured keratinocytes," Journal of Biological Chemistry, vol. 270, No. 21 (1995), pp. 12607-12613.
Sabolinski, M.L. et al., "Cultured skin as a 'smart material' for healing wounds: experience in venous ulcers," BIOMATERIALS, vol. 17, No. 3, (1996), pp. 311-320.
Hannappel, E., et al., "Actin-sequestering ability of thymosin B4, thymosin B4 fragments, and thymosin B4-like peptides as assessed by the Dnase I inhibition assay," Biol. Chem. vol. 374 (1993), pp. 117-122.
Jorneskog, K., et al., "Low molecular weight heparin seems to improve local capillary circulation and healing of chronic foot ulcers in diabetic patients," VASA, pp. 137-142, (1993).
Kubler, M. Dominique, et al., "Changes in the distribution of actin-associated proteins during epidermal wound healing", Journal of Investigative Dermatology, vol. 100, No. 6, (Jun. 1993), pp. 785-789.
Malinda, K.M., et al., "Thymosin β4 accelerates wound healing," Journal of Investigative Dermatology, vol. 113, No. 6, pp. 364-368, (Sep. 1999).
Cavasin, M.A., et al., "Prolyl oligopeptidase is involved in release of the antifibrotic peptide Ac-SDKP", Hypertension, May 2004; pp. 1-6; vol. 43.
Peng, H., et al., "Ac-SDKP reverses cardiac fibrosis in rats with renovascular hypertension", Hypertension, 42; Dec. 2003; pp. 1164-1170.
Philp, D., et al., "Thymosin β4 and a synthetic peptide containing its actin-binding domain promote demal wound repair in db/db diabetic mice and in aged mice", Wound Rep, and Regen, 11:1; 2003, pp. 19-24.
Philp, D., et al., "Thymosin β4 promotes angiogenesis, wound healing, and hair follicle development", Mech Ageing Dev., 125:2; 2004; pp. 113-115 (Abstract only).
Philp, D., et al., "The actin binding site of thymosin β4 promotes angiogenesis", The FASEB Jour., Sep. 18, 2003; 13 pages.
Philp, D., et al., "Thymosin β4 increases hair growth by activation of hair follicle stem cells", The FASEB Jour., Dec. 4, 2003; 16 pages.
Simenel, C., et al., "Structural requirements for thymosin β4 in its contact with actin: An NMR-analysis of thymosin β4 mutants in solution and correlation with their biological activity", Eur. J. Biochem., 267; 2000; pp. 3530-3538.
Yang, F, et al., "Ac-SDKP reverses inflammation and fibrosis in rats with heart failure after myocardial infarction", Hypertension, 43; Feb. 2004; pp. 229-236.
Vancompernolle, K., et al., "G- to F-actin modulation by a single amino acid substitution in the actin binding site of actobindin and thymosin β4", The EMBO Journal, 11:13; 1992; pp. 4739-4746.
Van Troys, M., et al., "The actin binding site of thymosin β4 mapped by mutational analysis", The EMBO Journal, 15:2; 1996; pp. 201-210.

* cited by examiner

*Primary Examiner*—B. Dell Chism
(74) *Attorney, Agent, or Firm*—Rothwell, Figg, Ernst & Manbeck, PC

(57) ABSTRACT

A composition with a polypeptide including amino acid sequence LKKTET [SEQ ID NO:1] or a conservative variant thereof, the composition further including a carrier for application to a surface of a body.

13 Claims, 11 Drawing Sheets

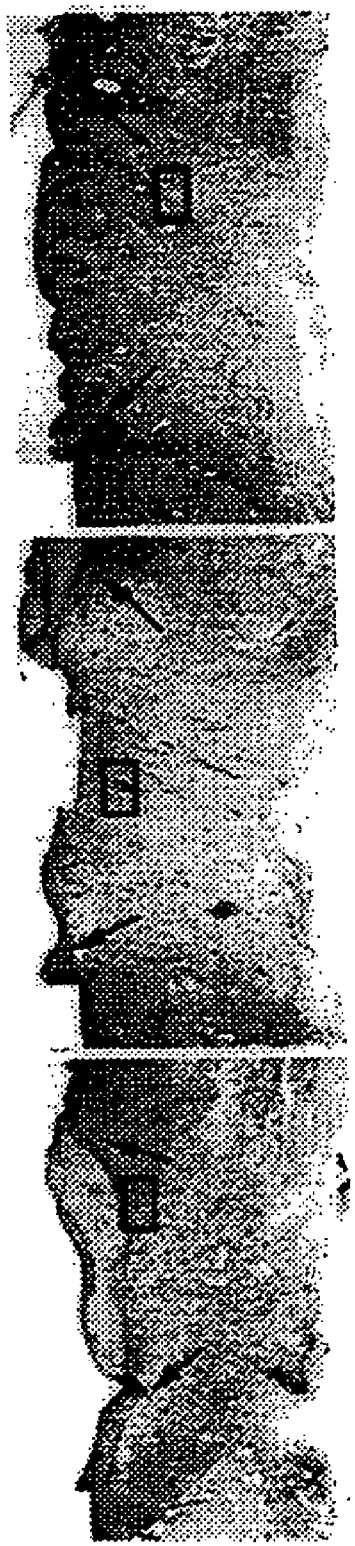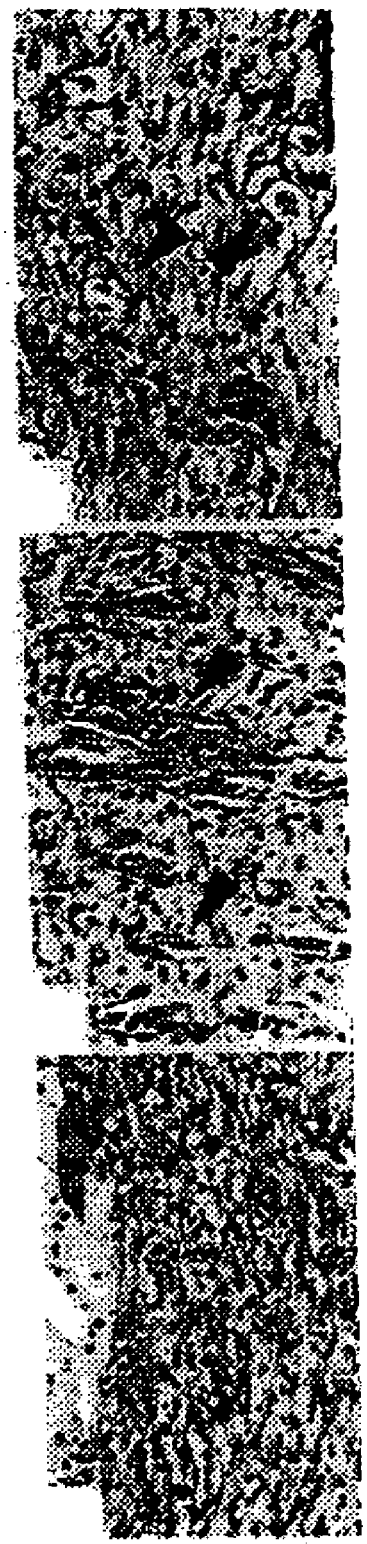
FIG. 4c  FIG. 4f
FIG. 4b  FIG. 4e
FIG. 4a  FIG. 4d

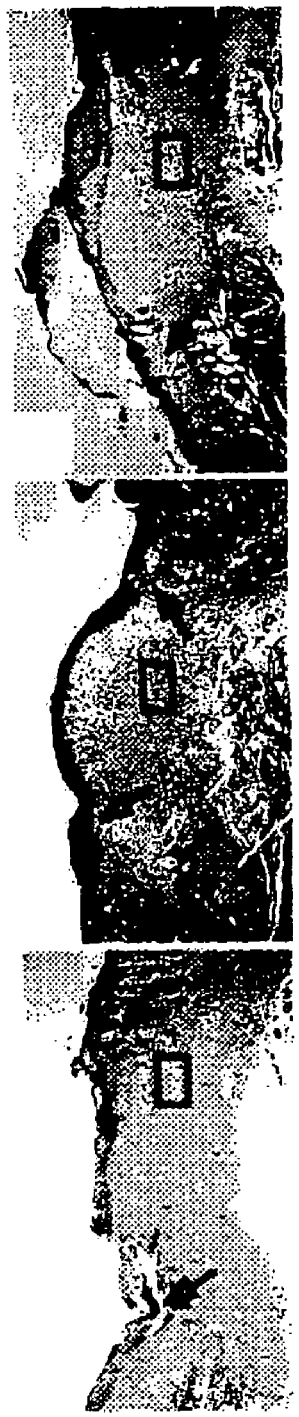

Amino Acid Sequence of Thymosin β4 and other β-Thymosins

```
                   5          10         15         20         25         30         35         40
              ....HELIX......                                          ....HELIX....
Tβ4           ac-SDKP DMAEI EKFDK SKLKK TETQE KNPLP SKETI EQEKQ AGES
Tβ4 Ala       ac-AKDP DMAEI EKFDK SKLKK TETQE KNPLP SKETI EQEKQ AGES
Tβ4 Xen       ac-SDKP DMAEI EKFDK SKLKK TETQE KNPLP SKETI EQEKQ STES
Tβ9           ac-ADKP DLGEI NSFDK AKLKK TETQE KNTLP TKETI EQEKQ AK
Tβ9 Met       ac-ADKP DMGEI NSFDK AKLKK TETQE KNTLP TKETI EQEKQ AK
Tβ10          ac-ADKP DMGEI ASFDK AKLKK TETQE KNTLP TKETI EQEKQ AK
Tβ11          ac-SDKP NLDEV ASFDK AKLKK TETQE KNTLP TKETI EQEKR SEIS
Tβ12          ac-SDKP DLAEV SNFDK TKLKK TETQE KNTLP TKETI EQEKQ AS
Tβ12 perch    ac-SDKP DISEV TSFDK TKLKK TETQE KNPLP SKETI EQEKQ ATA
Tβ13          ac-ADKP DMGEV ASFDK AKLKK TETQE KNTLP TKETI EQEKA AATS
Tβ14          ac-SDKP DISEV SSFDK TKLKK TETQE KNTLP TKETI EQEKQ AK
Tβ15          ac-SDKP DLSEV EIFDK SKLKK TETAE KNTLP TKETI EQELT A
Tβscallops    ac-SDKP FVSEV ANFDK SKLKK TNIEE KNTLP SKETI QQEKE YNQRS
Tβsea urch    ac-ADKP DVSEV STFDK SKLKK TETAE KNTLP TKETI QQEKE A
                                                                     TKDTI EQEKQ G
```

FIG. 11a

Phylogenetic Distribution of Thymosin $\beta_4$-Like Peptides

| Species | First peptide | Second peptide | Third peptide |
|---|---|---|---|
| Human | $\beta_4$ | $\beta_{10}$ | $\beta_{15}$ |
| Rat, mouse, cat | $\beta_4$ | $\beta_{10}$ | $\beta_{15}$ (rat tumor) |
| Calf | $\beta_4$ | $\beta_9$ | |
| Pig, sheep | $\beta_4$ | $\beta_9^{Met}$ | |
| Horse, chicken, gecko | $\beta_4$ | | |
| Xenopus laevis | $\beta_4^{Xen}$ | | |
| Rainbow trout | $\beta_{11}$ | $\beta_{12}$ | |
| Perch | $\beta_{12}^{perch}$ | | |
| Whale | $\beta_{13}$ | | |
| Sea urchin | $\beta_{14}$ | $\beta^{sea\ urchin}$ | |
| Scallop | $\beta^{scallop}$ | | |

FIG. 11b

THYMOSIN β4 COMPOSITIONS

This application is a continuation of U.S. application Ser. No. 09/772,445, filed Jan. 29, 2001, which is a continuation of PCT/US99/17282, filed Jul. 29, 1999, which claims benefit of U.S. Provisional Application No. 60/094,690, filed Jul. 30, 1998. The previously mentioned applications are explicitly incorporated herein by reference in their entirety for all purposes.

STATEMENT AS TO FEDERALLY SPONSORED RESEARCH

This invention was made in part with funds from the National Institutes of Health, Intramural Program. The government may have certain rights in this invention.

TECHNICAL FIELD OF THE INVENTION

The present invention relates generally to tissue repair and more specifically to methods of wound healing using thymosin β4.

BACKGROUND OF THE INVENTION

Inadequate methods and compositions to effectively heal chronic wounds is a significant health care problem. Impaired wound healing increases the chances of mortality and morbidity. This problem is especially prominent in patients with diabetes who develop severe, life threatening wounds on body extremities. Chronic diabetic foot ulcers often lead to amputations. These wounds are often the result of poor circulation derived from the diabetic patients' insulin-compromised cells as well as impaired vascularization of the wound bed, reduced infiltration of germ fighting cells and reduced tissue epithelialization. As a result, most current therapies include attempts to revascularize the wound bed and prevent infection.

Wounds in non-compromised tissues undergo a complex and ordered series of events to repair the tissue. The series of events may include infiltration of immune cells as part of the process to remove and destroy necrotic tissue, increased vascularization by angiogenic factors and increased cell proliferation and extracellular matrix deposition. Although the basic process of tissue repair has been characterized, the individual steps and factors necessary to carry out this complex series of events are not well understood. The identification of individual steps and factors could lead to improved methods for the treatment of diseases resulting from inadequate wound repair processes.

Previous studies have used the "scratch" wound closure assay to assess the potential effects of an agent on in vitro cell migration. Though informative, such a test does not mimic the dynamic in vivo wound healing conditions to the extent that not all factors involved in wound closure are present in the in vitro assay. For this reason, in vivo systems have been developed to assess the ability of an agent or factor to modulate wound healing activities.

Using these types of in vitro models, a number of specific growth factors have been recognized for their effect on angiogenesis. One such growth factor is TGF-β. This family of dimeric proteins includes TGF-β1, TGF-β2, TGF-β3, TGF-β4, and TGF-β5 which regulate the growth and differentiation of many cell types. This family of proteins exhibits a range of biological effects from stimulating the growth of some cell types (Noda et al., (1989) *Endocrinology*, 124:2991-2995) and inhibiting the growth of other cell types (Goey et al., (1989) *J. Immunol.*, 143:877-880; Pietenpol et al., (1990) *Proc. Nat'l. Acad. Sci. USA*, 87:3758-3762). TGF-β has also been shown to increase the expression of extracellular matrix proteins, including collagen and fibronectin (Ignotz et al., (1986) *J. Biol. Chem.*, 261:4337-4345) and accelerates the healing of wounds (Mustoe et al., (1987) *Science*, 237:1333-1335).

Another growth factor recognized for its effect on angiogenesis is Platelet Derived Growth Factor (PDGF). PDGF was originally found to be a potent mitogen for mesenchymal derived cells (Ross R. et al. (1974) *Proc Nat'l Acad Sci USA* 71(4):1207-1210.; Kohler N. et al. (1974) *Exp. Cell Res*. 87:297-301). Further studies have shown that PDGF increases the rate of cellularity and granulation in tissue formation. Wounds treated with PDGF have the appearance of an early stage inflammatory response, including an increase in neutrophils and macrophage cell types at the wound site. These wounds also show enhanced fibroblast function (Pierce, GF et al. (1988) J. Exp. Med. 167:974-987). Both PDGF and TGFβ have been shown to increase collagen formation, DNA content, and protein levels in animal studies. (Grotendorst, GR et al. (1985) *J. Clin. Invest.* 76:2323-2329.; Sporn, MB et al. (1983) *Science* 219:1329). The effect of PDGF in wound healing has been shown to be effective in human wounds. In human wounds, PDGF-AA expression is increased within pressure ulcers undergoing healing. The increase of PDGF-AA corresponds to an increase in activated fibroblasts, extracellular matrix deposition, and active vascularization of the wound. Furthermore, such an increase in PDGF-AA is not seen in chronic non-healing wounds. A number of other growth factors having the ability to induce angiogenesis and wound healing include, Vascular Endothelial Growth Factor (VEGF), Keratinocyte Growth Factor (KGF) and basic Fibroblast Growth Factor (bFGF).

However, most of these growth and angiogenic factors have side effects. Accordingly, there is a need for additional factors useful in promoting wound repair.

SUMMARY OF THE INVENTION

The present invention is based on the discovery that thymosin β4 (Tβ4) accelerates wound healing and stimulates wound repair. Based on this finding, it is now possible to develop methods for accelerating wound healing in subjects having wounds in need of such treatment.

In a first embodiment, the invention provides a method for promoting wound repair in a subject in need of such treatment by administering to the subject or contacting the site of the wound with a wound-healing effective amount of a composition containing a wound healing polypeptide comprising the amino acid sequence LKKTET [SEQ ID NO:1] and conservative variants thereof having wound healing activity. In one aspect of the method, the wound healing polypeptide is Tβ4 or an isoform of Tβ4.

In another embodiment, the invention provides a method for promoting tissue repair in a tissue in need of such treatment by contacting the tissue with an effective amount of a composition containing a wound healing polypeptide comprising the amino acid sequence LKKTET [SEQ ID NO:1] and conservative variants thereof having wound healing activity, or nucleic acid encoding a wound healing polypeptide. In one aspect of the method, a wound healing peptide is Tβ4 or an isoform of Tβ4. The tissue may be contacted either in vivo or ex vivo.

In yet another embodiment, the invention provides a method of modulating wound repair in a subject in need of such treatment by systemic delivery of a wound-healing effective amount of a wound healing polypeptide comprising the amino acid sequence LKKTET [SEQ ID NO:1] and conservative variants thereof having wound healing activity. In one aspect of the method, a wound healing peptide is Tβ4 or an isoform of Tβ4.

In yet another embodiment, the present invention provides a method for stimulating epithelial cell migration at the site of a wound by contacting the wound with an effective amount of a Tβ4 polypeptide.

In another embodiment, the invention provides a method of diagnosing a pathological condition in a subject characterized by a wound healing disorder associated with Tβ4, including obtaining a sample suspected of containing Tβ4 from the subject, detecting a level of Tβ4 in the sample and comparing the level of Tβ4 with the level found in a normal sample (i.e., a standard sample).

In another embodiment, the invention provides a method of ameliorating a wound healing disorder associated with Tβ4, including treating a subject having the disorder with a composition which modulates Tβ4 activity or the activity of a Tβ4 isoform.

In yet another embodiment, the present invention provides pharmaceutical compositions comprising a wound healing polypeptide comprising the amino acid sequence LKKTET [SEQ ID NO:1] and conservative variants thereof having wound healing activity and a pharmaceutically acceptable carrier. In one aspect, the wound healing polypeptide is Tβ4 or an isoform of Tβ4.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a histological section, stained with H&E, demonstrating the appearance of control and thymosin β4 treated wounds at low magnification and higher magnification. Wounds are from day 7 as described in the legend to FIG. 2. Arrows indicate the edges of the original wound. (A) Control wound treated with saline. Migration of the epithelium is visible at the wound edges and debris are visible over the unhealed wound. (B) Increased re-epithelialization of the wound occurred when Tβ4 was injected intraperitoneally (60 µg/300 µl on alternate days). (C) Topical treatment (5 µg/50 µl of Tβ4) resulted in complete reepithelialization of the wound epidermis. Boxed areas are the location of the higher magnification fields (D-F). (D-F) Dermis near dermal and epidermal junction. (D) Control showing few cells near the dermis and little neovascularization. (E) and (F) Dermis showing granulation tissue infiltrated with fibroblasts and extensive neovascularization (arrowheads). (E) Intraperitoneal treatment and (F) topical application both resulted in significant new capillaries. (Scale bar=1 mm).

FIG. 5 shows histological sections of 7 day wounds showing collagen deposition/accumulation. Masson's trichrome staining shows collagen and endothelial cells. (A) Low magnification view of a control wound treated with saline. (B) and (C). Low magnification views of wounds where Tβ4 was injected intraperitoneally (B) or applied topically (A). Boxed areas are the location of the higher magnification fields (D-F). Arrows indicate the edges of the original wound. (D) Control wound at higher magnification showing baseline collagen accumulation. Treatment intraperitoneally (E) or (F) topically resulted in enhanced collagen production/accumulation compared to wounds treated with saline. (Scale bar=1 mm).

FIG. 11 shows the amino acid sequence of several known isoforms their phylogenetic distribution [Tβ$_4$:SEQ ID NO:2, Tβ$_4^{Ala}$:SEQ ID NO:3, Tβ$_4^{XEN}$:SEQ ID NO:4, Tβ$_9$:SEQ ID NO:5, Tβ$_9^{Met}$:SEQ ID NO:6, Tβ$_{10}$:SEQ ID NO:7, Tβ$_{11}$:SEQ ID NO:8, Tβ$_{12}$:SEQ ID NO:9, Tβ$_{12}^{Perch}$:SEQ ID NO:10, Tβ$_{13}$:SEQ ID NO:11, Tβ$_{14}$:SEQ ID NO:12, Tβ$_{15}$:SEQ ID NO:13, Tβ$^{Scallops}$:SEQ ID NO:14, Tβ$^{sea\ urch}$:SEQ ID NO:15]. N-terminal acetylation is indicated by "ac." Residues between 13 and 24 are thought to be important for actin binding.

DETAILED DESCRIPTION OF THE INVENTION

Figure 1:
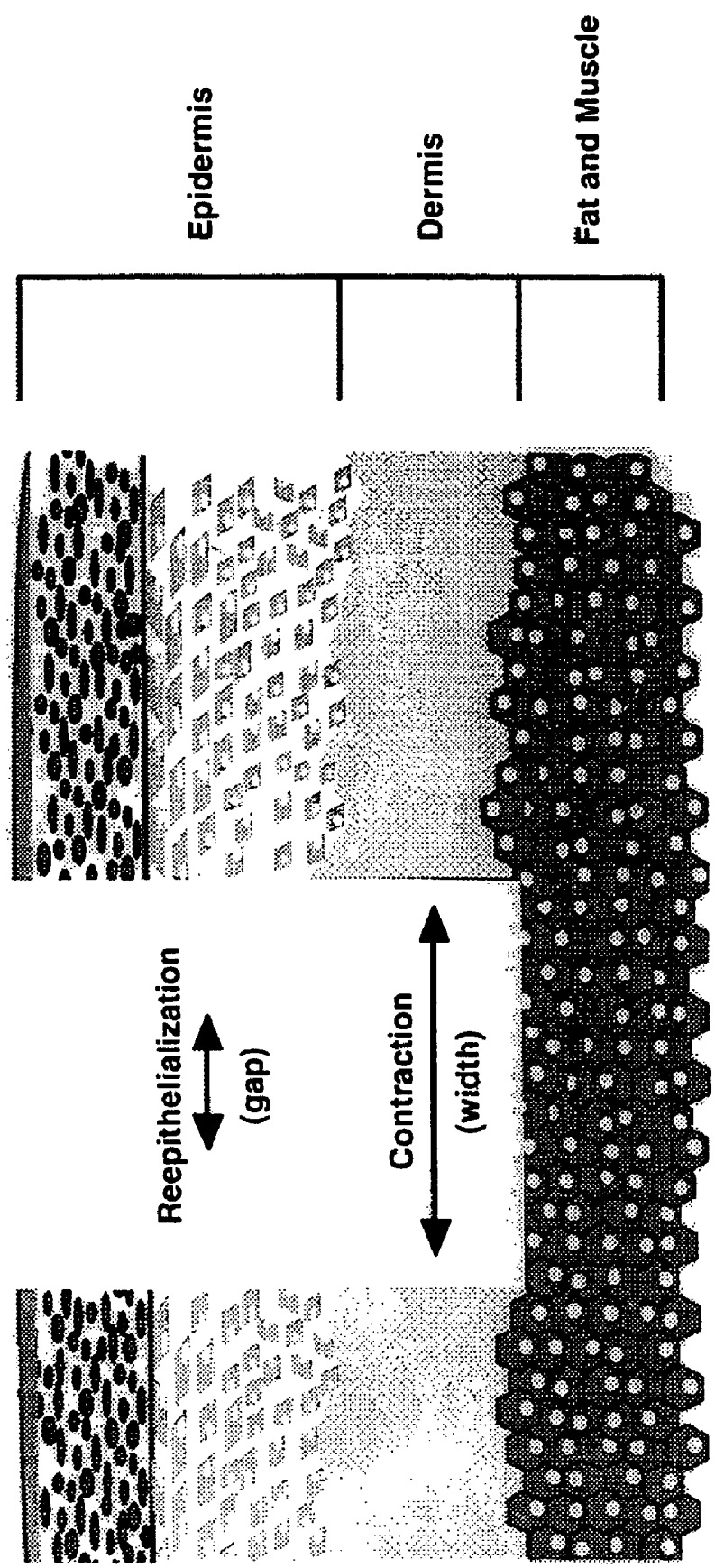
FIG. 1 is a schematic drawing of a wound.

Thymosin β4 was initially identified as a protein that is up regulated during endothelial cell migration and differentiation in vitro. Thymosin β4 was originally isolated from the thymus and is a 43 amino acid, 4.9 kDa ubiquitous polypeptide identified in a variety of tissues. Several roles have been ascribed to this protein including a role in endothelial cell differentiation and migration, T cell differentiation, actin sequestration and vascularization. One biological activity of thymosin β4 (Tβ4), as shown herein, effects tissue repair and wound healing. Another activity of Tβ4 is anti-inflammatory activity.

The present invention resulted from investigation of the effects of Tβ4 on wound healing. In vivo results have demonstrated that topical and systemic delivery of Tβ4 promotes wound healing. Additional experiments demonstrated that Tβ4-treated wounds have increased extracellular matrix deposition in the wound bed.

The present invention identifies Tβ4 as an active factor in promoting wound closure and tissue repair in vivo as well as increasing epithelial cell migration. In vivo administration of Tβ4 indicates that cell migration, angiogenesis and extracellular matrix deposition are stimulated at or above the levels observed for migration, angiogenesis and matrix deposition in control animals. Tβ4 promotes wound closure when administered systemically (e.g., intra-peritoneally) and topically in wounded animal models. Increased levels of collagen were also observed in treated wounds showing that Tβ4 treatment can also accelerate wound contraction and stimulate the healing process.

The methods of the invention result from the identification of the effect of Tβ4 on wound healing. In vivo, Tβ4 stimulates wound healing in a full thickness punch wound (see Example 1) and in repair of eye-related wounds (Example 4). When given either topically or systemically (e.g., intra-peritoneally) Tβ4 accelerated closure and healing of wounds (see Example 1, 4, and 5).

Promoting Tissue Regeneration

In one embodiment, the invention provides a method for accelerating wound healing in a subject by contacting a wound with a wound-healing effective amount of a composition which contains Tβ4 or a Tβ4 isoform. The contacting may be topically or systemically. Examples of topical administration include, for example, contacting the wound with a lotion, salve, gel, cream, paste, spray, suspension, dispersion, hydrogel, ointment, or oil comprising Tβ4. Systemic administration includes, for example, intravenous, intraperitoneal, intramuscular injections of a composition containing Tβ4 or a Tβ4 isoform. A subject may be any mammal, preferably human.

In addition, Tβ4 or a Tβ4 isoform is therapeutically valuable in cases where there is an impaired wound healing process, such as in wound healing compromised subjects. By "wound healing compromised" is meant subjects which have a reduced, decreased, or inability to recover from a wounding or trauma, due to recurrent wounding, trauma or inability of the subject's natural system to properly effectuate wound healing. For example, steroids reduce the ability of a subject to heal as compared to a subject which is not on steroids. Other such wounds present in compromised subjects include, but are not limited to, skin wounds such as diabetic ulcers, venus ulcers or pressure ulcers. Additionally, Tβ4 or a Tβ4 isoform is therapeutically valuable to augment the normal healing process.

As used herein, a "wound-healing effective amount" of a composition containing Tβ4 or a Tβ4 isoform for use in wound healing is defined as that amount that is effective in promoting tissue regeneration and repair. The "wound-healing effective amount" may be the therapeutically effective amount. Diseases, disorders or ailments possibly modulated by Tβ4 or a Tβ4 isoform include tissue repair subsequent to traumatic injuries or conditions including arthritis, osteoporosis and other musculo-skeletal disorders, burns, ulcers and other skin lesions, neurological and nerve disease and cardiovascular diseases including ischemia and atherosclerosis. Other potential tissues which can be treated by the methods and compositions of the invention include epidermal, eye, uro-genital, gastro-intestinal, cardiovascular, muscle, connective, and neural tissues. The term "induce", "induction" or "effect" as used herein, refers to the activation, stimulation, enhancement, initiation and/or maintenance of cellular mechanisms or processes necessary for the formation of a tissue or a portion thereof, repair process or tissue development as described herein.

Modulation of Wound Healing

Wound healing, tissue regeneration and tissue repair result from a complex process that includes the proliferation and migration of inflammatory cells, endothelial cells, stromal cells and parenchymal cell, the deposition of extracellular matrix materials and the growth of new blood vessels, particularly capillaries. This complex process plays a crucial role in such beneficial functions as embryogenesis, the female reproductive cycle, as well as such abnormal functions as arthritis, chronic ulcerations and neuro-degenerative diseases.

In another embodiment, the invention provides a method for modulating wound healing in a subject or a tissue including contacting the subject or tissue with an effective wound-healing amount of a composition containing Tβ4 or a Tβ4 isoform. It is envisioned that Tβ4 or a Tβ4 isoform can be administered topically or systemically to prevent or treat a damaged tissue including, for example, tissues damaged due to ischemia, including ischemic brain, bone and heart disease, damage to corneal or retinal tissue of the eye, and damage to epithelial tissue, including skin.

In addition, the method of the invention is useful in promoting wound healing in tissues by promoting angiogenesis in tissue deprived of adequate blood flow. For example, a composition containing Tβ4 can promote the healing of chronic ulcers by increasing blood supply to the tissue site as well as increasing keratinocyte migration to close a wound.

Figure 10A:
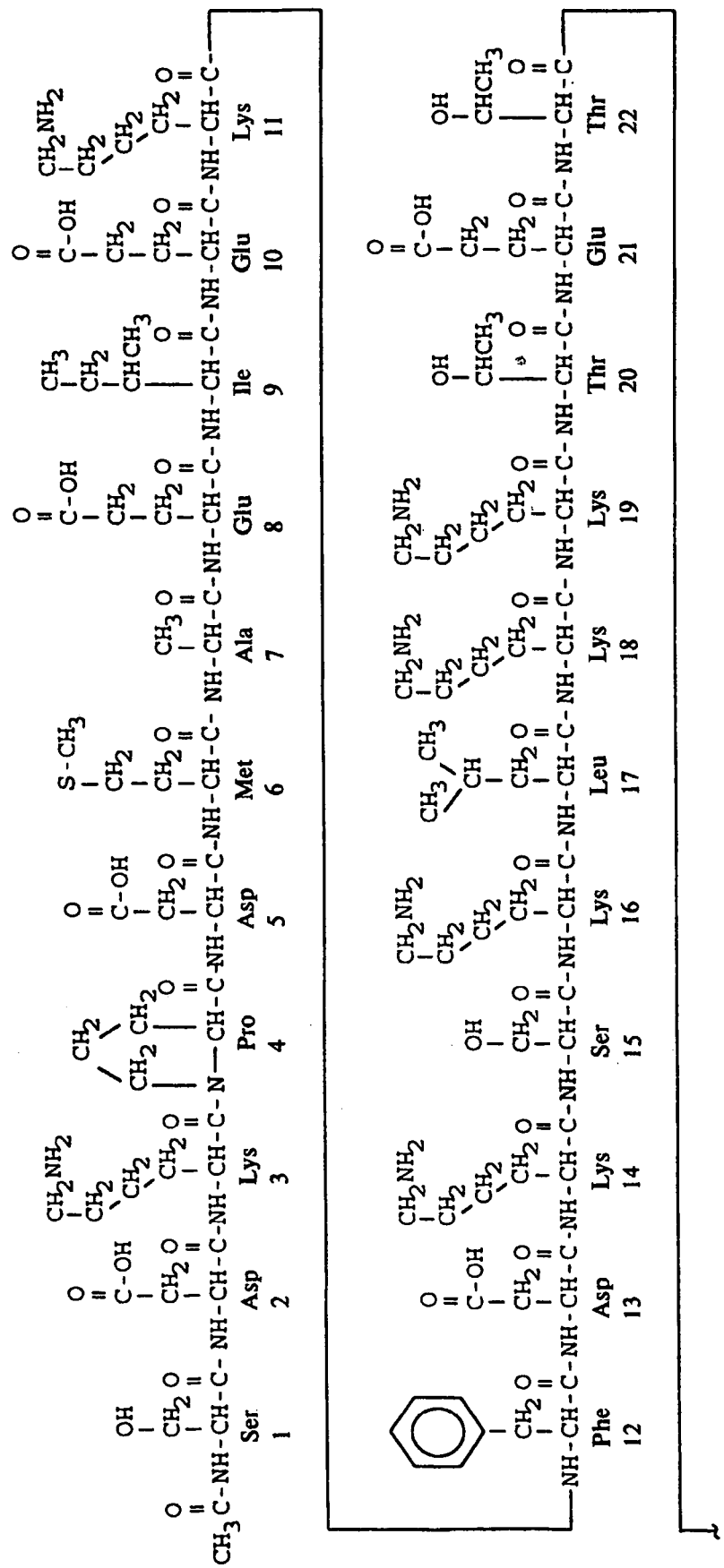
FIG. 10 shows an amino acid sequence of Tβ4 [SEQ ID NO:2.]
Figure 10B:
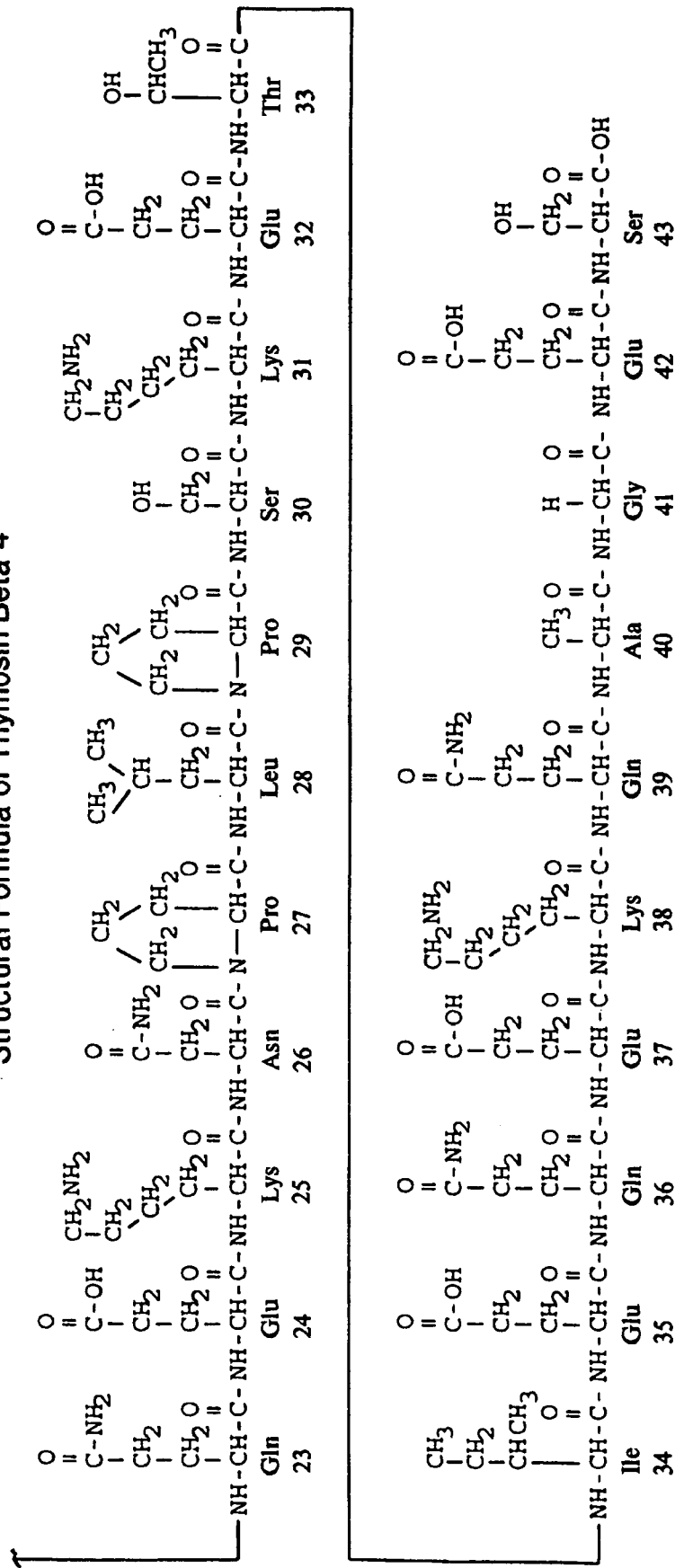

Tβ4 isoforms have been identified and have about 70%, or about 75%, or about 80% or more homology to the amino acid sequence of Tβ4 set forth in FIG. 10. Such isoforms include, for example, Tβ4$^{ala}$, Tβ9, Tβ10, Tβ11, Tβ12, Tβ13, Tβ14 and Tβ15 (FIG. 11; see also, Mihelic etal., (1994) Amino Acids, 6:1-13, which describes the amino acid sequence of other Tβ4 isoforms, and is incorporated herein by reference). Similar to Tβ4, the Tβ10, and Tβ15 isoforms have been shown to sequester actin. Tβ4, Tβ10 and Tβ15, as well as these other isoforms share an amino acid sequence, LKKTET [SEQ ID NO:1], that appears to be involved in mediating actin sequestration or binding. Although not wishing to be bound to any particular theory, the wound healing activity of Tβ4 and Tβ4 isoforms may be due, in part, to the ability to polymerize actin. For example, Tβ4 can modulate actin polymerization in wounds to promote healing (e.g., β-thymosins appear to depolymerize F-actin by sequestering free G-actin). Tβ4's ability to modulate actin polymerization may therefore be due to all, or in part, its ability to bind to or sequester actin via the LKKTET [SEQ ID NO:1] sequence. Thus, as with Tβ4, other proteins which bind or sequester actin, or modulate actin polymerization, including Tβ4 isoforms having the amino acid sequence LKKTET [SEQ ID NO:1], are likely to promote wound healing alone, or in a combination with Tβ4, as set forth herein.

Thus, it is specifically contemplated that known Tβ4 isoforms, such as Tβ4$^{ala}$, Tβ9, Tβ10, Tβ11, Tβ12, Tβ13, Tβ14, and Tβ15, as well as Tβ4 isoforms not yet identified, will be useful in the methods of the invention. As such Tβ4 isoforms are useful in the methods of the invention, including the methods practiced in a subject, the invention therefore further provides pharmaceutical compositions comprising Tβ4 isoforms Tβ4$^{ala}$, Tβ9, Tβ10, Tβ11, Tβ12, Tβ13, Tβ14, and Tβ15 and a pharmaceutically acceptable carrier.

In addition, other proteins having actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET [SEQ ID NO:1], for example, can similarly be employed in the methods of the invention. Such proteins including gelsolin, vitamin D binding protein (DBP), profilin, cofilin, depactin, Dnase1, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, Dnase1, vilin, fragmin, severin, capping protein, β-actinin and acumentin as set forth herein. Thus, the invention includes the use of wound healing polypeptide comprising the amino acid sequence LKKTET [SEQ ID NO:1] and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of Tβ4 can be added to a composition to effect Tβ4 production from a tissue and/or a cell. Agents that effect wound repair can also be included in such a composition to augment the wound healing process. Such agents include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the agent is transforming growth factor beta (TGF-β) or other members of the TGF-β superfamily. Tβ4 compositions of the invention aid in wound healing by effectuating growth of the connective tissue through extracellular matrix deposition, cellular migration and vascularization of the wound bed.

Additionally, agents that assist or stimulate the wound healing process may be added to a composition along with Tβ4 or a Tβ4 isoform to further modulate the wound healing process. Such agents include angiogenic agents, growth factors, agents that direct differentiation of cells, agents that promote migration of cells and agents that stimulate the provision of extracellular matrix materials in the wound bed. For example, and not by way of limitation, Tβ4 or a Tβ4 isoform alone or in combination can be added in combination with any one or more of the following agents: VEGF, KGF, FGF, PDGF, TGFβ, IGF-1, IGF-2, IL-1, prothymosin α and thymosin α1 in a wound-healing effective amount.

In another aspect, the invention is useful for repair of tissue resulting from injuries due to surgical procedures, irradiation, laceration, toxic chemicals, viral infections, bacterial infections or burns. Additionally, the invention is useful for revitalizing scar tissue resulting from any number of procedures, accidents or trauma. The term "scar tissue" means fibrotic or collagenous tissue formed during the healing of a wound or other morbid process. For example, Tβ4 can be included in a controlled release matrix which can be positioned in proximity to damaged tissue thereby promoting regeneration, repair and/or revascularization of such tissue. The term "controlled release matrix" means any composition that allows for the release of a bioactive substance which is mixed or admixed therein. The matrix can be a solid composition, a porous material (such as a scaffold, mesh, or sponge), or a semi-solid, gel or liquid suspension containing bioactive substances. The term "bioactive material" means any composition that modulates tissue repair when used in accordance with the method of the present invention. The bioactive materials or matrix can be introduced by means of injection, surgery, catheters or any other means suitable for modulating tissue repair.

It is envisioned that the methods and compositions of the invention can be used to aid wound healing and repair in guided tissue regeneration (GTR) procedures. Such procedures are currently used by those skilled in the medical arts to accelerate wound healing. Typically, nonresorbable or bioabsorbable materials are used to accelerate wound healing by promoting the repopulation of the wound area with cells which form the architectural and structural matrix of the tissue. For example, the methods and compositions of the invention can be used in aiding tissue repair or regeneration at an ulcer site in a human or other subject by placing a composition containing a bioreasorbable polymer and Tβ4 at the site in need of tissue repair or regeneration such that the composition is effective for aiding tissue regeneration by releasing a wound-healing effective amount of Tβ4 at the site.

In another aspect, the invention is useful for the purposes of promoting tissue growth during the process of tissue engineering. As used herein, "tissue engineering" is defined as the creation, design, and fabrication of biological prosthetic devices, in combination with synthetic or natural materials, for the creation, augmentation or replacement of body tissues and organs. Thus, the present method can be used to augment the design and growth of human tissues outside the body, for later implantation inside the body, or augment the design and growth of a tissue inside the body to repair or replace diseased or damaged tissue. For example, Tβ4 may be useful in promoting the growth of skin graft replacements which are used as a therapy in the treatment of burns and ulcers.

In another aspect of tissue engineering, Tβ4 can be included in external or internal devices containing human tissue designed to replace the function of a diseased internal tissue. This approach involves isolating cells from the body, placing them on or within a three-dimensional matrices and implanting the new system inside the body or using the system outside the body. The methods and compositions of the invention can be used and included in such matrices to promote the growth of tissues contained in the matrices. For example, Tβ4 can be included in a tissue engineered construct to promote the growth of the cells contained in the construct. It is envisioned that the method of the invention can be used to augment tissue repair, regeneration and engineering in endothelial cell-related products which may contain cartilage, cartilage-bone composites, bone, central nervous system tissues, muscle, liver, pancreatic islet (insulin-producing) cells, urogenital tissues, breast and tissues for gene therapy applications.

The present invention further provides methods and compositions for modulating female reproductive tract function. Growth factors have been shown to play a role in cyclic mitosis and differentiation of endometrial cellular components, recruitment of macrophages in decidualizing the endometrium, endometrial-trophoblast interactions, early pregnancy maintenance, and endometrial functional regeneration. The term "modulate" as used herein, denotes a modification of an existing condition or biologic state. Modulation of a condition as defined herein, encompasses both an increase or a decrease in the determinants affecting the existing condition. For example, administration of Tβ4 could be used to augment uterine functions in a condition where the promotion of endothelial cell growth is desired. For example, the uterus may be treated with Tβ4 to promote the growth and development of placental membranes or endometrial growth or the repair of these tissue following tissue injury. Furthermore, treatment with Tβ4 may be used to promote and maintain a pregnancy by facilitating endometrial-trophoblast interaction. Alternatively, antagonist to Tβ4 could be administered to modulate conditions of excessive endometrial growth in which the level of Tβ4 is excessive in comparison to a normal biological condition. In addition, Tβ4 in combination with other agents, such as thymosin α1, may be desirable for treating disorders of the reproductive tract.

The therapeutic approaches described herein involve various routes of administration or delivery of reagents or compositions comprising the Tβ4 of the invention including any conventional administration techniques (for example, but not limited to, topical administration, local injection, inhalation, or systemic administration), to a subject with a wound or tissue in need of healing or repair. Administration of Tβ4, as described above, can accelerate wound healing, increase cell migration into a wound site, induce the formation of tissue repair or regeneration, or promote the growth and development of the endometrium. The reagent, formulation or composition may also be targeted to specific cells or receptors by any method described herein or by any method known in the art of delivering, targeting Tβ4 polypeptides and expressing genes encoding Tβ4. For example, the methods and compositions using or containing Tβ4 of the invention may be formulated into pharmaceutical compositions by admixture with pharmaceutically acceptable non-toxic excipients or carriers. Such compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Sustained release compositions are also encompassed by the present invention. Compositions for other routes of administration may be prepared as desired using standard methods.

A composition of the invention containing Tβ4 may be conveniently administered in unit dosage form, and may be prepared by any of the methods well known in the pharmaceutical art, for example, as described in *Remington's Pharmaceutical Sciences* (Mack Pub. Co., Easton, Pa, 1990). Formulations for parenteral administration may contain as common excipients sterile water or saline, polyalkylene glycols such as polyethylene glycol, oils of vegetable origin, hydrogenated naphtalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as a gel to be applied intranasally. Formulations for parenteral administration may also include glycocholate for buccal administration.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidyl-choline.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The therapeutic agents useful in the method of the invention can be administered parenterally by injection or by gradual perfusion over time. Administration may be intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a pharmaceutical composition comprising a therapeutically effective amount of Tβ4 or a Tβ4 isoform in a pharmaceutically acceptable carrier. Such carriers include those listed above with reference to parenteral administration.

The actual dosage or reagent, formulation or composition that modulates a tissue repair process, fibrotic disorder, a sclerotic disorder, a cell proliferative disorder, or wound healing depends on many factors, including the size and health of a subject. However, one of ordinary skill in the art can use the following teachings describing the methods and techniques for determining clinical dosages (Spilker B., *Guide to Clinical Studies and Developing Protocols*, Raven Press Books, Ltd., New York, 1984, pp. 7-13, 54-60; Spilker B., *Guide to Clinical Trials*, Raven Press, Ltd., New York, 1991, pp. 93-101; Craig C., and R. Stitzel, eds., *Modern Pharmacology*, 2d ed., Little, Brown and Co., Boston, 1986, pp. 127-33; T. Speight, ed., *Avery's Drug Treatment: Principles and Practice of Clinical Pharmacology and Therapeutics*, 3d ed., Williams and Wilkins, Baltimore, 1987, pp. 50-56; R. Tallarida, R. Raffa and P. McGonigle, *Principles in General Pharmacology*, Springer-Verlag, New York, 1988, pp. 18-20) or to determine the appropriate dosage to use.

Antibodies that Bind to Tβ4

Antibodies to Tβ4 peptide or fragments could be valuable as diagnostic tools to aid in the detection of diseases in which Tβ4 is a pathological factor. Further, use of antibodies which bind to Tβ4 and inhibit or prevent the actions of Tβ4 are included in the present invention. Therapeutically, antibodies or fragments of the antibody molecule could also be used to neutralize the biological activity of Tβ4 in diseases where Tβ4 is over expressed. Such antibodies can recognize an epitope of Tβ4 or fragments thereof suitable for antibody recognition and neutralization of Tβ4 activity. As used in this invention, the term "epitope" refers to an antigenic determinant on an antigen, such as a Tβ4 peptide, to which the paratope of an antibody, such as an Tβ4-specific antibody, binds. Antigenic determinants usually consist of chemically active surface groupings of molecules, such as amino acids or sugar side chains, and can have specific three-dimensional structural characteristics, as well as specific charge characteristics.

Preparation of an antibody requires a substantially purified moiety that can provide an antigenic determinant. The term "substantially pure" as used herein refers to Tβ4, or variants thereof, which is substantially free of other proteins, lipids, carbohydrates or other materials with which it is naturally associated. Substantially purified or "isolated" refers to molecules, either nucleic or amino acid sequences, that are removed from their natural environnent, isolated or separated, and are at least 60% free, preferably 75% free, and most preferably 90% free from other components with which they are naturally associated. One skilled in the art can isolate Tβ4 or a Tβ4 isoform using standard techniques for protein purification. The substantially pure peptide will yield a single major band on a non-reducing polyacrylamide gel. The purity of the Tβ4 peptide can also be determined by amino-terminal amino acid sequence analysis. Tβ4 or a Tβ4 isoform peptide includes functional fragments of the peptide, as long as the activity of Tβ4 or a Tβ4 isoform remains. Smaller peptides containing the biological activity of Tβ4 or a Tβ4 isoform are included in the invention. As used in the present invention, the term "antibody" includes, in addition to conventional antibodies, such protein fragments that have the ability to recognize specifically and bind the Tβ4 protein or variants thereof. Regions of the gene that differ at the protein level are well defined. A protein can be raised by expression of the wild type (wt) gene or of the variants, or, preferably, fractions therefore. For example, the nucleic acid sequence can be cloned into expression vectors. According to this embodiment, the sequence of interest can first be obtained by employing PCR, as described above, or from a synthetic gene construction with overlapping and ligated synthetic oligonucleotides. Another alternative would involve synthesis of a short peptide. All those methodologies are well known to one skilled in the art. See, for example, Ausubel et al., CURRENT PROTOCOLS IN MOLECULAR BIOLOGY, Volumes 1 and 2 (1987), with supplements, and Maniatis et al, MOLECULAR CLONING, A LABORATORY MANUAL, Cold Spring Harbor Laboratory, all of which are incorporated herein by reference.

The invention provides a method for detecting Tβ4, or variants thereof, which includes contacting an anti-Tβ4 antibody with a sample suspected of containing Tβ4, (e.g., cell or protein) and detecting binding to the antibody. An antibody which binds to Tβ4 peptide is labeled with a compound which allows detection of binding to Tβ4. There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation. For purposes of the invention, an antibody specific for Tβ4 peptide may be used to detect the level of Tβ4 in biological fluids and tissues. Any specimen containing a detectable amount of antigen can be used. The level of Tβ4 in the suspect cell can be compared with the level in a normal cell to determine whether the subject is predisposed to a Tβ4 associated increase in angiogenesis or wound healing.

Use of antibodies for the diagnostic methods of the invention includes, for example, immunoassays in which the antibodies can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Tβ4 antibodies can be bound to many different carriers and used to detect the presence of an antigen comprising the peptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

The invention includes use of antibodies immunoreactive with Tβ4 peptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and F(ab')$_2$, Fv and SCA fragments which are capable of binding an epitopic determinant on Tβ4.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

Alternatively, a therapeutically or diagnostically useful anti-Tβ4 antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86: 3833 (1989), which is hereby incorporated in its entirety by reference. Techniques for producing humanized monoclonal antibodies are described, for example, by Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993), which are hereby incorporated by reference.

Antibodies of the invention also may be derived from human antibody fragments isolated from a combinatorial immunoglobulin library. See, for example, Barbas et al, METHODS: A COMPANION TO METHODS IN ENZYMOLOGY, VOL. 2, page 119 (1991); Winter et al., Ann. Rev. Immunol. 12: 433 (1994), which are hereby incorporated by reference. Cloning and expression vectors that are useful for producing a human immunoglobulin phage library can be obtained, for example, from STRATAGENE Cloning Systems (La Jolla, Calif.).

Methods and Compositions for Treating or Diagnosing Tβ4-Associated Disorders

In another embodiment of the invention, a method of diagnosing a pathological state in a subject suspected of having a pathology characterized by a disorder associated with Tβ4 is provided. The method includes obtaining a sample suspected of containing Tβ4 from the subject, determining the level of Tβ4 in the sample and comparing the level of Tβ4 in the sample to the level of Tβ4 in a normal standard sample. Such conditions include, but are not limited to subjects having cell proliferative disorders, recurrent wounds, tissue repair disorders, fibrotic tissue disorders, chronic ulcers and other disorders described herein. Such disorders further include those associated with the various Tβ4 isoforms, known or not yet identified.

The term "cell-proliferative disorder" denotes malignant as well as non-malignant cell populations which often appear to differ from the surrounding tissue both morphologically and genotypically. Malignant cells (i.e. cancer) develop as a result of a multistep process. Such disorders may be detected using the methods of the current invention. For example, a sample suspected of containing Tβ4 is obtained from a subject, the level of Tβ4 peptide is determined and compared with the level of Tβ4 peptide in a normal tissue sample. The level of Tβ4 can be determined by any number of methods including, for example, immunoassay using anti-Tβ4 peptide antibodies. Other variations of such assays include radioimmunoassay (RIA), ELISA and immunofluorescence. Alternatively, nucleic acid probes can be used to detect and quantify Tβ4 peptide mRNA for the same purpose. Such detection methods are standard in the art.

In another embodiment, the invention provides a method for ameliorating a wound healing disorder associated with Tβ4 or a Tβ4 isoform, including treating a subject having the disorder with a composition that regulates Tβ4 activity. The term "ameliorate" denotes a lessening of the detrimental effect of the disease-inducing response in the subject receiving therapy. Where the disease is due to an abnormally high level of Tβ4, the administration of an agent, such as an antagonist of Tβ4 activity, may be effective in decreasing the amount of Tβ4 activity. Alternatively, where the disease is due to an abnormally low level of Tβ4, the administration of Tβ4 or an agent that increases Tβ4 activity, such as an agonist, may be effective in increasing the amount of Tβ4 activity.

In yet another embodiment, the invention provides a method of treating a subject having a wound healing disorder characterized by recurrent or slow to heal wounds or wounds that are chronic non-healing wounds associated with altered Tβ4 or Tβ4 isoform gene expression in a subject. The method includes administering to a subject having the disorder a wound-healing effective amount of an agent which modulates Tβ4 gene expression, thereby treating the disorder. The term "modulate" refers to inhibition or suppression of Tβ4 expression when Tβ4 is over expressed, and induction of expression when Tβ4 is under expressed. The term "wound-healing effective amount" means that amount of Tβ4 agent which is effective in modulating Tβ4 gene expression resulting in reducing the symptoms of the Tβ4 associated wound healing disorder.

An agent which modulates Tβ4 or Tβ4 isoform gene expression may be a polynucleotide for example. The polynucleotide may be an antisense, a triplex agent, or a ribozyme. For example, an antisense may be directed to the structural gene region or to the promoter region of Tβ4 may be utilized.

When a wound healing disorder is associated with the expression of Tβ4, a therapeutic approach which directly interferes with the translation of Tβ4 mRNA into protein is possible. For example, an antisense nucleic acid or a ribozyme can be used to bind to the Tβ4 RNA or to cleave it. Antisense RNA or DNA molecules bind specifically with a targeted gene's RNA message, interrupting the expression of that gene's protein product. The antisense binds to the mRNA forming a double stranded molecule which cannot be translated by the cell. Antisense oligonucleotides of about 15-25 nucleotides are preferred since they are easily synthesized and have an inhibitory effect just like antisense RNA molecules. In addition, chemically reactive group, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal., Biochem.*, 172:289, 1988).

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target Tβ4 producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species.

These and other uses of antisense methods to inhibit the in vivo translation of genes are well known in the art (e.g., De Mesmaeker, et al., 1995. Backbone modifications in oligonucleotides and peptide nucleic acid systems. *Curr. Opin. Struct. Biol.* 5:343-355; Gewirtz, A. M., et al., 1996b. Facilitating delivery of antisense oligodeoxynucleotides: Helping antisense deliver on its promise; *Proc. Natl. Acad. Sci.* U.S.A. 93:3161-3163; Stein, C. A. A discussion of G-tetrads 1996. Exploiting the potential of antisense: beyond phosphorothioate oligodeoxynucleotides. *Chem. and Biol.* 3:319-323).

Delivery of antisense, triplex agents, ribozymes, competitive inhibitors and the like can be achieved using a recombinant expression vector such as a chimeric virus or a colloidal dispersion system. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR, These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

A targeted delivery system for delivery of nucleic acids as described herein includes a colloidal dispersion system. Colloidal dispersion systems include macromolecule complexes, nanocapsules, microspheres, beads, gene activated matrices and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

Pathologically, Tβ4 may be involved in diseases in which there is an overgrowth of blood vessels, such as cancer, tumor formation and growth, diabetic retinopathy, neovascular glaucoma, rheumatoid arthritis and psoriasis.

The ingrowth of capillaries and ancillary blood vessels is essential for growth of solid tumors and is thus an unwanted physiological response which facilitates the spread of malignant tissue and metastases. Inhibition of angiogenesis and the resultant growth of capillaries and blood vessels is therefore a component of effective treatment of malignancy in use of treatment of cancer patients.

Thus, in another embodiment, the invention provides a method of inhibiting angiogenesis in a subject, including administering to the subject a composition containing an agent which regulates Tβ4 activity. The composition may include agents that regulate angiogenesis, for example agents that affect thymosin α1, PDGF, VEGF, IGF, FGF and TGFβ. For example, the inhibition of angiogenesis and endothelial cell migration can be beneficial in controlling the growth of solid tumors. Most, if not all solid tumors, like normal tissue, require a steady and sufficient blood supply for optimal growth. Tumors are known to make use of angiogenic growth factors to attract new blood vessels and ascertain supply with sufficient amounts of nutrients to sustain their growth. Many tumors are well vascularized and the inhibition of the formation of an adequate blood supply to the tumor by inhibition of tumor vascularization, as a result of inhibition of angiogenesis, is beneficial in tumor growth control. Without a strong blood supply, rapid and prolonged growth of tumor tissue cannot be sustained. Thus, agents that inhibit Tβ4 activity may be used to prevent neoplastic growth. The Tβ4 inhibiting agent may be administered orally, parenterally, topically, intravenously, or systemically. In addition, for inhibiting tumor cell proliferation and tumor growth the agent may be administered locally directly to the tumor or as a part of a deposited slow release formulation. Administration may be on a daily basis for as long as needed to inhibit angiogenesis, endothelial cell proliferation, tumor cell proliferation or tumor growth. Alternatively, a slow release formulation may continue for as long as needed to control tumor growth. This dosage regimen may be adjusted to provide the optimum therapeutic response. For example, several divided doses may be administered daily or the dose may be proportionally reduced as indicated by the exigencies of the therapeutic situation.

In this regard, the compositions of this invention that are useful as inhibitors of angiogenesis, endothelial cell proliferation, tumor cell proliferation and tumor growth contain a pharmaceutically acceptable carrier and an amount of Tβ4 modulating agent effective to inhibit tumor or endothelial cell proliferation. Such compositions may also include preservatives, antioxidants, immunosuppressants and other biologically and pharmaceutically effective agents which do have effects on tumor growth but which do not exert a detrimental effect on the Tβ4 modulating agent. For treatment of tumor cells the composition may include a chemotherapeutic agent, for example an anti-cancer agent which selectively kills the faster replicating tumor cells, many of which are known and clinically used. Exemplary anticancer agents include mephalan, cyclophosphamide, methotrexate, adriamycin and bleomycin.

Screen for Compounds which Modulate Tβ4 Activity

In another embodiment, the invention provides a method for identifying a compound that modulates Tβ4 activity, angiogenesis activity or wound healing activity. The method includes incubating components including the compound and Tβ4 under conditions sufficient to allow the components to interact and determining the effect of the compound on Tβ4 activity before and after incubating in the presence of the compound. Compounds that affect Tβ4 activity (e.g., antagonists and agonists) include peptides, peptidomimetics, polypeptides, chemical compounds, minerals such as zincs, and biological agents. Tβ4 activity can be assayed using the methodology as described in the present Examples.

The present Examples are meant to illustrate, but not limit the scope of the appended claims. Accordingly, one skilled in the art will recognize a number of equivalent materials and methods, which are intend to be covered by the present invention and disclosure.

EXAMPLE 1

In vivo Wound Healing is Accelerated by Tβ4

Figure 2A:
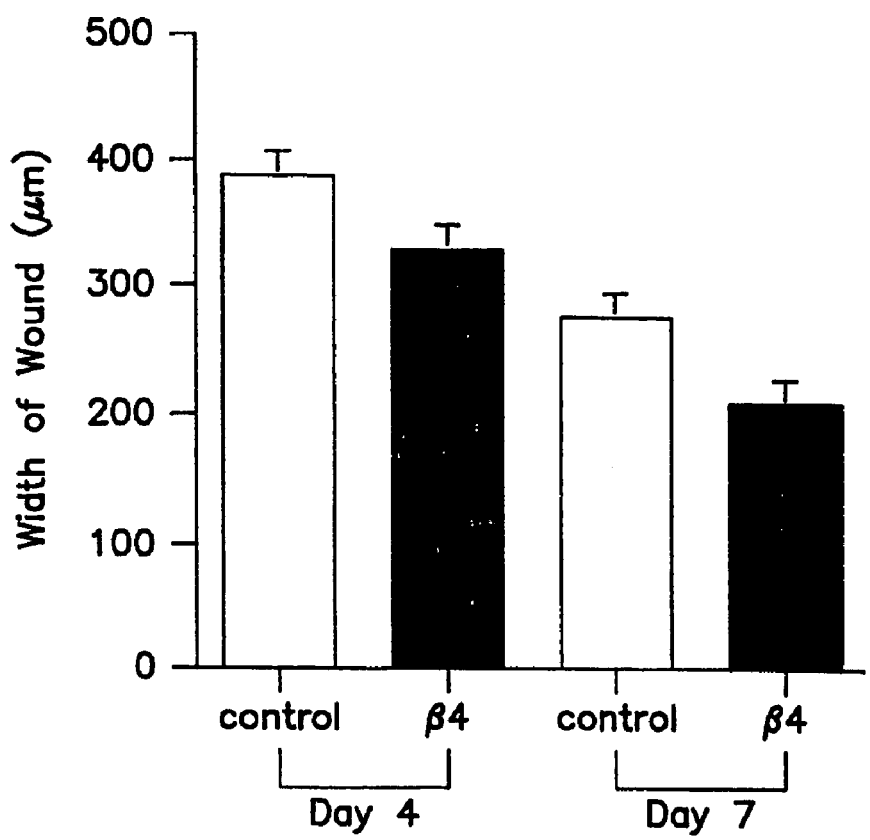
FIG. 2 is a bar graph which shows the effect of topical and systemic delivery of Tβ4 on the width of a punch wound as compared to control. (A) Topical delivery of 5 µg/50 µl was performed on three of the six wounds in each animal on the day of wounding and at 48 hours after wounding. (B) Intraperitoneal injections of 60 µg/300 µl were done on the day of the wounding and thereafter every other day. Control animals were treated similarly with saline. Measurements are expressed as the mean percent decrease ± SEM.
Figure 2B:
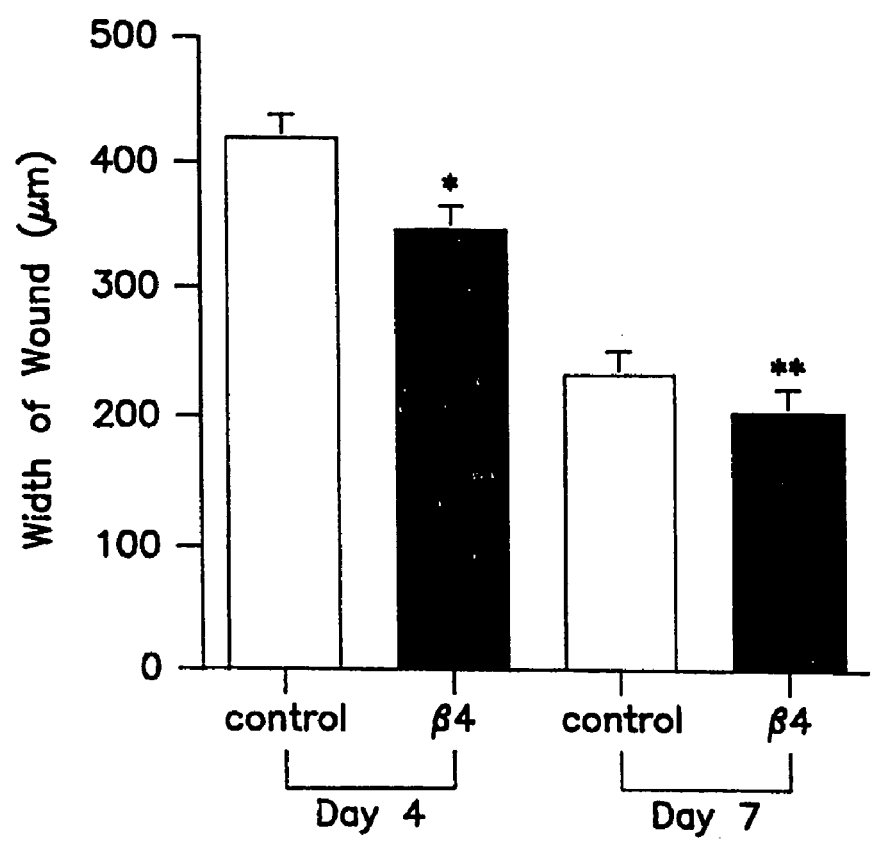
Figure 3A:
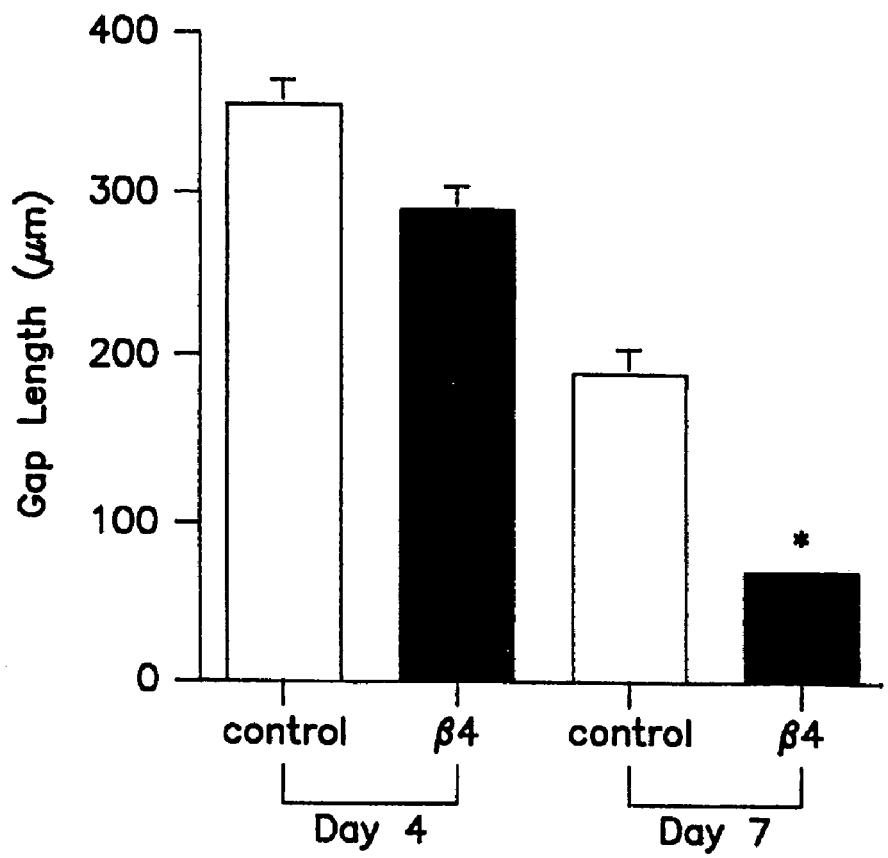
FIG. 3 is a bar graph which shows the effect of topical and systemic delivery of Tβ4 on the gap of a punch wound as compared to control. (A) Topical delivery of 5 µg/50 µl was performed on the day of wounding and at 48 hours after wounding. (B) Intraperitoneal injections of 60 µg/300 µl were done on the day of the wounding and thereafter every other day. Measurements are expressed as the mean percent decrease ± SEM.
Figure 3B:
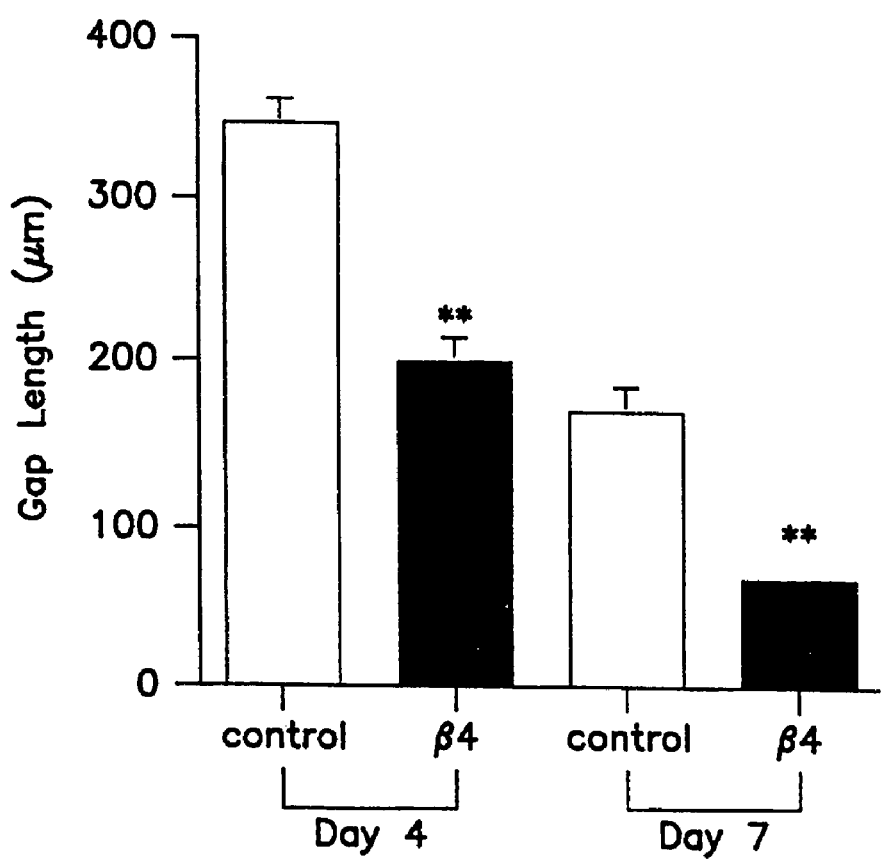

Tβ4, whether administered topically or intraperitoneal, significantly accelerated wound healing as compared to untreated wounds (FIGS. 2 and 3). Full thickness 8 mm punch biopsy wounds were made on the dorsal surface of rats as previously reported (Bhartiya et al., *J. Cell. Physiol.* 150:312, 1992; Sihhu et al., *J. Cell. Physiol.* 169:108, 1996) and Tβ4 was given topically at the time of wounding (5 µg in 50 µl) and again after 48 hours. Controls for the topical treatment received identical amounts of saline at the time of wounding and at 48 hours. Additional rats received intraperitoneal injections at the time of wounding (60 µg in 300 µl) and again every other day (e.g., days 0, 2, 4, and 6). Controls for these animals received identical amounts of saline intraperitoneally on the same injection schedule. On days 4 and 7 post-wounding, measurements were made on the wound size. At days 8 and 9 post-wounding, tissue was collected and fixed in 10% buffered formalin. The samples were sectioned and stained with H&E and Masson's Trichrome (American Histolabs, Gaithersburg, Md.).

Histological sections were used to measure the re-epithelialization and the contraction of the wound using an ocular micrometer. Epidermal migration was determined by measuring the lengths of the tongues of epithelium migrating form either side of the wound over the wound bed from the zone of proliferation at the margin of the uninjured and wounded skin. Epidermal thickness was also measured beginning at the junction of the uninjured and proliferating epidermis. The thickness was measured vertically from the basement membrane to the most superficial layer of the migrating epidermis at every 200 microns. The mean epidermal thickness of each migrating tongue of epidermis was then computed from each wound. Vessel counts were performed by first identifying vascular spaces by their endothelial lining. All such vessels in the wound bed were counted including those at the junction of the dermis and the subcutis, since angiogenesis into the wounds occurs to a great extent from these vessels. The numbers were averaged into vessel counts per 10 high powered fields (40×).

The effect of Tβ4 on wound healing was studied in a full thickness cutaneous rat wound model. FIG. 1 shows a diagram of the wound site that extends form the epidermis to the fat/muscle layer. This model allowed measurement of two parameters: the re-epithelialization (gap) and the contraction (width) of the wound. Wounds treated topically with Tβ4 showed about a 15% decrease in width and about 15% decrease in gap in the treated versus controls (FIGS. 2 and 3, respectively).

FIG. 2 shows a 15% decrease in wound width as compared to the saline controls as early as 4 days after wounding and continued until day 7. Intraperitoneal injection of Tβ4 resulted in a 18% decrease in wound width relative to saline treated controls at day 4 and 11% decrease at day 7. This trend was observed on the 4th day post wounding and continued through day 7 (*$P \leq 0.0001$, **$P \leq 0.08$, significant difference from media alone, student's t-test). These data demonstrate that Tβ4, when given either topically or systemically, increases wound re-epithelialization and contraction. Both topical and systemic treatment are equally effective. Lower doses of Tβ4 were tested including 2.5 μg and 0.5 μg in 50 μl for topical and 30 μg and 6 μg in 300 μl for intraperitoneal injection but reduced or no effect, respectively, was observed on wound healing.

FIG. 3 shows an 18% decease in gap length as compared to saline controls when Tβ4 is administered topically, as early as 4 days after wounding. This trend continued to termination at day 7 (*$P \leq 0.04$, student's t-test). Intraperitoneal injections resulted in a 42% decrease in gap size relative to saline treated controls. This decrease was observed on the 4th day post wounding and continued through day 7 (**$P \leq 0.0007$, student's t-test). The increase in re-epithelialization was observed in wounds treated for 7 days and the rate of gap closure was slightly accelerated over that observed at day 4. A 62% decrease in gap size was observed in the Tβ4-treated wounds. Quantitation of epidermal migration showed a statistically significant 1.5 fold increase in migration of epidermal tongues over the wound bed after topical treatment (Table 1). Quantitation of epithelial migration in intraperitoneally treated wounds showed a statistically significant increase in migration of epidermal tongues as compared to controls (Table 1). There was no difference in the thickness of the migrating epidermis between either of the Tβ4 treatments and the control (Table 1). Histological sections of the wounds clearly show increased re-epithelialization in the treated wounds as compared to controls in 7 day wounds (FIG. 4).

TABLE 1

Morphometric Measurements of Control and Thymosin β4 Treated Samples

| Parameter | Control | I.P. | Topical |
|---|---|---|---|
| Epidermal Migration (μm) | 2403.3 ± 9.7 | 3168.3 ± 38.4* | 3668.7 ± 56.6* |
| Epidermal Thickness (μm) | 128.2 ± 19.3 | 135.0 ± 11.7 | 142.3 ± 19.8 |
| Vessels/ 10 HPF | 1364.0 ± 15.0 | 2415.0 ± 24.3* | 2186.0 ± 11.8* |

HPF: high power field.
*$P \leq 0.00001$ by Welch's t-test, significantly different than control.

FIG. 4 shows a comparison of typical control (D) and Tβ4-treated (E and F) sections of 7 day wounds. Treatment with Tβ4 resulted in considerable capillary ingrowth (FIGS. 4E and F, arrows). Vessel counts showed a significant (about 2 fold) increase in the number of vessels in Tβ4 treated wounds (Table 1). No increases in the number of macrophages in the wounds were observed. There was no apparent increase in the accumulation/biosynthesis of collagen in treated –Tβ4 wounds (FIGS. 5B and C vs A) supporting a decreased wound width and supporting a role for Tβ4 in wound contraction. Both the topical and systemically treated wound appeared similar although the wound contraction proceeded slightly more quickly with the topical treatment.

Reduction of the wound size was observed in both experimental groups as compared to control groups (FIG. 2-4). More and larger blood vessels were noted in the experimental groups as compared to the controls (FIG. 4). Additionally, an increase in the accumulation/biosynthesis of collagen by Tβ4 treated wounds as compared to control suggests a role for Tβ4 in wound contraction and extracellular matrix deposition. Histological staining of these wounds demonstrated an increase in collagen density and extracellular matrix deposition when compared to controls. (FIG. 5).

EXAMPLE 2

Migration Assays of Keratinocytes

Primary keratinocytes were prepared from either Balb/c or CD-1 newborn mice as described previously (Dlugosz et al., 1995). Cells were plated in calcium- and magnesium-free Eagle's Minimal Essential Medium (EMEM) containing 8% fetal calf serum treated with 8% Chelex (Bio-Rad Laboratories, Hercules, Calif.), 20 units/ml penicillin-streptomycin, and the calcium concentration was adjusted to 0.25 mM. The following day, cultures were washed with calcium- and magnesium-free phosphate buffered saline, treated briefly with Trypsin (Life Technologies, Gaithersburg, Md.), washed with culture medium and resuspended in EMEM containing 0.05 mM calcium. Cells were used immediately in migration assays.

Keratinocyte migration assays were carried out in Boyden chamber using 12 μm pore polyester membranes (Poretics, Livermore, Calif.) coated with a 0.1 mg/ml solution of collagen IV in $dH_2O$ (Trevigen, Gaithersburg, Md.). Filters were then dried at least 1 h. Cells were harvested using Versene or Trypsin (Life Technologies, Gaithersburg, Md.) and resuspended in Eagle's minimal essential medium with 0.05 mM $Ca^{2+}$. The bottom chamber was loaded with EMEM containing 0.01, 0.1, 10, 100, and 1000 ng/ml of synthetic Tβ4. Conditioned medium from primary dermal fibroblasts and/or keratinocyte growth factor was added to several wells as a positive control. Cells were added to the upper chamber at a concentration of 50,000 cells per well. Chambers were incubated at 35 C/7% $CO_2$ for 4-5 hours and the filters were then fixed and stained using Diff-Quik (Baxter Healthcare Corporation, McGraw Park, Ill.). The cells that migrated through the filter were quantitated by counting the center of each well at 10× using an Olympus CK2 microscope. Each condition was assayed in triplicate wells and each experiment was repeated four times with different preparations of cells.

Figure 6:
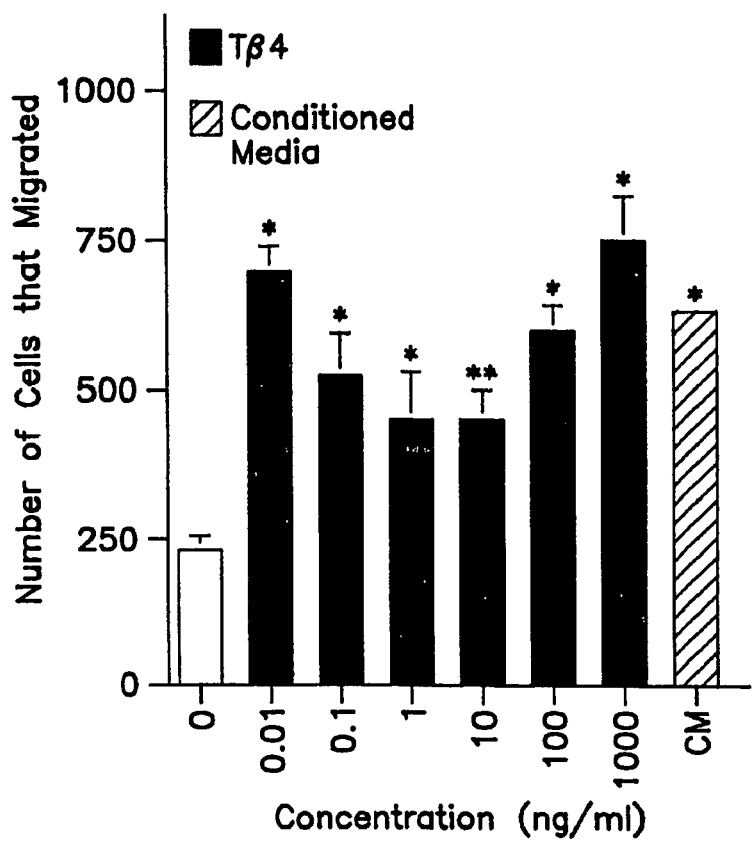
FIG. 6 shows Tβ4 stimulated keratinocyte migration in Boyden chamber assays. (A) Tβ4 in the lower wells of the chamber resulted in a 2-3 fold increase in migration on filters coated with collagen IV. The positive control, conditioned media, also showed increased migration over media alone.

The results demonstrated that keratinocyte migrated in response to Tβ4 after 4-5 hours of exposure. Migration was enhanced 2-3 fold ($P \leq 0.003$) over migration in the presence of media alone (FIG. 6) and at the maximal responding dose exceeded the positive control. The effect of Tβ4 on migration, while showing slightly different dose curves depending on the cell preparation and source, clearly showed a biphasic pattern with 1000 ng/ml and 0.01 ng/ml showing the most migration and the middle doses showing less stimulation (but still greater than control media) in all 4 assays.

EXAMPLE 3

Migration Assays of Corneal Epithelial Cells

Figure 7:
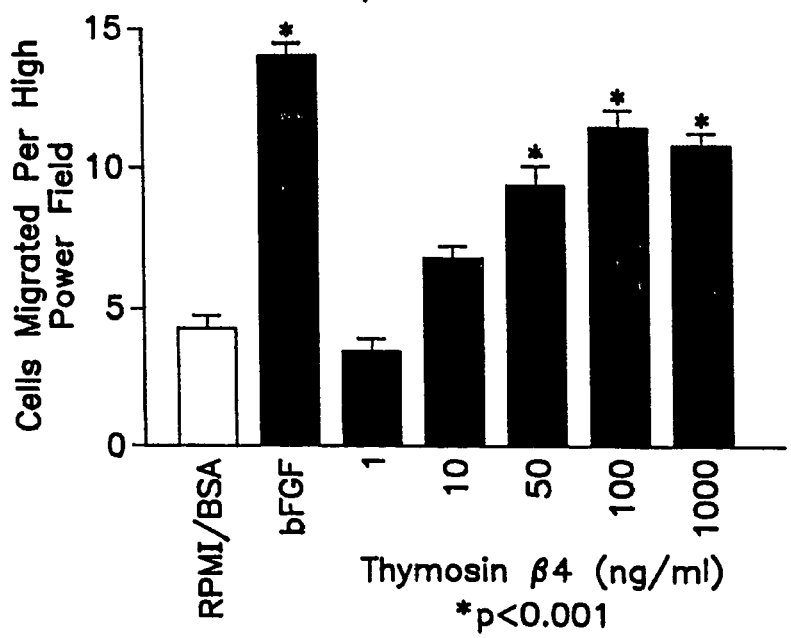
FIG. 7 shows a graph demonstrating the migration of corneal epithelial cells at various concentrations of Tβ4.

Corneal Epithelial Cell migration assays were carried out in Boyden chamber using 12 μm pore polyester membranes (Poretics, Livermore, Calif.) coated with a 0.1 mg/ml solution of collagen IV in $dH_2O$ (Trevigen, Gaithersburg, Md.). Filters were then dried at least 1 h. Cells were cultured and resuspended in Eagle's Minimal Essential Medium with 0.05 mM $Ca^{2+}$. The bottom chamber was loaded with EMEM containing 0.01, 0.1, 10, 100, and 1000 ng/ml of synthetic Tβ4. Conditioned medium from primary dermal fibroblasts and/or keratinocyte growth factor was added to several wells as a positive control. Cells were added to the upper chamber at a concentration of 50,000 cells per well. Chambers were incubated at 35 C/7% $CO_2$ for 4-5 hours and the filters were then fixed and stained using Diff-Quik (Baxter Healthcare Corporation, McGraw Park, Ill.). The cells that migrated through the filter were quantitated by counting the center of each well at 10× using an Olympus CK2 microscope. Each condition was assayed in triplicate wells and each experiment was repeated four times with different preparations of cells. The results demonstrated that corneal epithelial cell migrated in response to Tβ4 after 4-5 hours of exposure. Migration was enhanced 2-3 fold over migration in the presence of media alone (FIG. 7) with the highest level of migration seen at 100 ng/ml of Tβ4.

EXAMPLE 4

In vivo Corneal Re-Epithelialization

Figure 8:
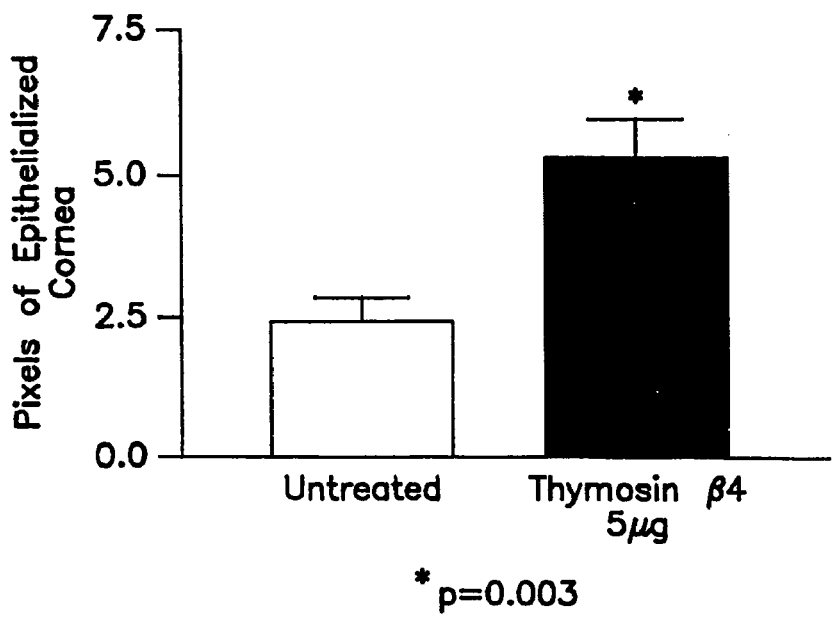
FIG. 8 shows a graph representing corneal re-epithelialization in rat corneas in the presence and absence of Tβ4.
Figure 9:
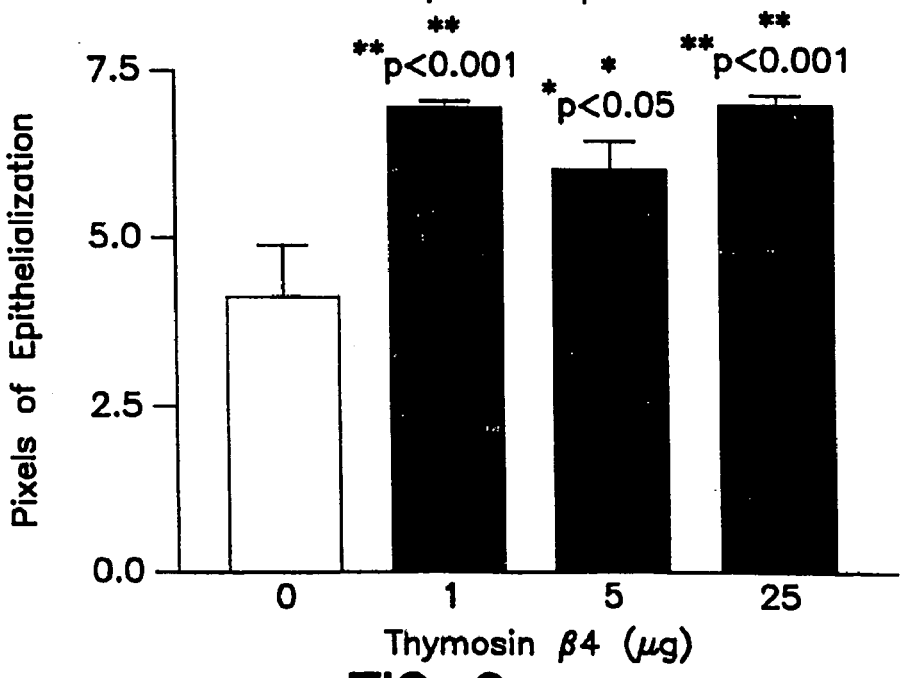
FIG. 9 shows a graph representing corneal re-epithelialization in the presence and absence of various concentrations of Tβ4.

To determine the effect of Tβ4 on corneal re-epithelialization in vivo, Rat corneas were de-epithelialized and treated with Tβ4. Filters were soaked in heptanol, applied to the eye for 30 seconds, and then the epithelium was scraped. Various concentration of Tβ4 in saline was applied to the eye and at 24 hours the rats were sacrificed. The eyes were fixed, sectioned and the degree of corneal epithelial migration (as measured in pixels) was determined using a microscope with an internal caliper by a masked observer. The results demonstrate that re-epithelialization of the cornea was increased 2-fold over untreated control in the presence of about 1 to 25 μg of Tβ4 (FIGS. 8 and 9). In addition, it was noted that Tβ4 treated eyes had reduced inflammation compared to the non-treated corneas.

EXAMPLE 5

Impaired Healing Model

Thymosin β4 also enhanced wound healing in an impaired model. Steroid treatment reduces the rate of wound repair in mammals. Rats treated with steroids such as hydrocortisone serve as a model of impaired wound healing due to the delay observed in wound closure. Animals were injected intramuscularly everyday with hydrocortisone. Steroid treated rats showed a significant increase in the level of healing when Tβ4 was added topically or injected intraperitoneally. At the initial time point, day 4, topically treated animals showed little response ($\leq$7% gap or width closure, N=3) compared to saline treatment. Intraperitoneal injection, however, resulted in a 28% decrease in3 gap size and a 14% decrease in wound width. At day 7, a response was observed with both topical treatment and intraperitoneal injection.

The gap in topically treated animals decreased by 39% compared to saline treatment. The wound width decreased by 23%. Intraperitoneal injection resulted in a 26% decrease in gap size and a 10% decease in wound width. Taken together, these demonstrate that Tβ4 is useful to treat chronic, as well as, acute wounds.

A number of embodiments of the present invention have been described. Nevertheless, it will be understood that various modifications may be made without departing from the spirit and scope of the invention. Accordingly, other embodiments are within the scope of the following claims.

The invention claimed is:

1. A composition comprising a polypeptide comprising amino acid sequence LKKTET [SEQ ID NO:1] or a conservative variant thereof, the composition further comprising a carrier for application to a surface of human body, wherein said carrier is for application to an external surface of said body or to an internal surface of said body, the composition comprising a gel, cream, paste, lotion, spray, suspension, dispersion, salve, hydrogel or ointment, wherein said polypeptide is gelsolin, vitamin D binding protein (DBP), profilin, cofilin, depactin, DnaseI, villin, fragmin, severin, capping protein, beta- actinin, acumentin, TB4, TB4ala, TB9, TB10, TB11, TB12, TB13, TB14, or TB15, wherein said polypeptide is at a concentration in said carrier of at least about 0.01 ng/ml, and up to about 60 micrograms per 300 microliter.

2. The composition of claim 1 wherein said carrier is a matrix.

3. The composition of claim 1 wherein said carrier is for application to an internal surface of said body.

4. The composition of claim 3 wherein said carrier is for oral or nasal administration.

5. The composition of claim 1 wherein said carrier is for administration to an external surface of said body.

6. The composition of claim 5 wherein said carrier is a topical carrier.

7. A composition comprising a polypeptide agent consisting essentially of TB4, TB4ala, TB9, TB10, TB11, TB12, TB13, TB14, or TB15, the composition further comprising a carrier for application to a surface of a human body, wherein said carrier is for application to an external surface of said body or to an internal surface of said body, the composition comprising a gel, cream, paste, lotion, spray, suspension, dispersion, salve, hydrogel or ointment, wherein said polypeptide is at a concentration in said carrier of at least about 0.01 ng/ml, and up to about 60 micrograms per 300 microliter.

8. The composition of claim 7 wherein said carrier is a matrix.

9. The composition of claim 7 wherein said carrier is for application to an internal surface of said body.

10. The composition of claim 9 wherein said carrier is for oral or nasal administration.

11. The composition of claim 10 wherein said carrier is for application to an external surface of said body.

12. The composition of claim 7 wherein said polypeptide consists essentially of TB4.

13. The composition of claim 12 wherein said carrier is for application to an external surface of said body.

* * * * *

UNITED STATES PATENT AND TRADEMARK OFFICE
CERTIFICATE OF CORRECTION

| | | |
|---|---|---|
| PATENT NO. | : 7,268,118 B2 | Page 1 of 1 |
| APPLICATION NO. | : 10/853505 | |
| DATED | : September 11, 2007 | |
| INVENTOR(S) | : Hynda K. Kleinman et al. | |

It is certified that error appears in the above-identified patent and that said Letters Patent is hereby corrected as shown below:

Figure 11a, line 5:
    change "T$\beta_4$ ac-SDKP DMAEI EKFDK SKLKK TETQE KNPLP SKETI EQEDQ AGES"
    to --T$\beta_4$ ac-SDKP DMAEI EKFDK SKLKK TETQE KNPLP SKETI EQEKQ AGES--

Claim 1, Col. 28, line 59:
    change "Dnase I, villin" to --DNaseI, vilin--

Claim 1, Col. 28, line 60:
    change "beta- actinin" to --beta-actinin--

Claim 1, Col. 28, lines 60-61:
    change "TB4, TB4ala, TB9, TB10, TB11, TB12, TB13, TB14, or TB15," to
    --T$\beta$4, T$\beta$4$^{ala}$, T$\beta$9, T$\beta$10, T$\beta$11, T$\beta$12, T$\beta$13, T$\beta$14, or T$\beta$15,--

Claim 7, Col. 29, lines 10-11:
    change "TB4, TB4ala, TB9, TB10, TB11, TB12, TB13, TB14, or TB15," to
    --T$\beta$4, T$\beta$4$^{ala}$, T$\beta$9, T$\beta$10, T$\beta$11, T$\beta$12, T$\beta$13, T$\beta$14, or T$\beta$15,--

Claim 12, Col. 30, line 13:
    change "TB4" to --T$\beta$4--

Signed and Sealed this
Fourth Day of October, 2011

David J. Kappos
*Director of the United States Patent and Trademark Office*

SEQUENCE LISTING

<160> NUMBER OF SEQ ID NOS: 15

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2
<211> LENGTH: 43
<212> TYPE: PRT
<213> ORGANISM: Homo sapiens

<400> SEQUENCE: 2

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

-continued

Thr Ile Glu Gln Glu Asp Gln Ala Gly Glu Ser
        35                  40

<210> SEQ ID NO 3
<211> LENGTH: 43
<212> TYPE: PRT
<213> ORGANISM: Homo sapiens

<400> SEQUENCE: 3

Ala Lys Asp Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40

<210> SEQ ID NO 4
<211> LENGTH: 43
<212> TYPE: PRT
<213> ORGANISM: Xenopus laevis

<400> SEQUENCE: 4

Ser Asp Lys Pro Asp Met Ala Glu Ile Glu Lys Phe Asp Lys Ala Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ser Thr Glu Ser
        35                  40

<210> SEQ ID NO 5
<211> LENGTH: 41
<212> TYPE: PRT
<213> ORGANISM: Bos taurus

<400> SEQUENCE: 5

Ala Asp Lys Pro Asp Leu Gly Glu Ile Asn Ser Phe Asp Lys Ala Lys
1               5                   10                  15

Leu Lys Lys Thr Glu Thr Gln Glu Lys Asn Thr Leu Pro Thr Lys Glu
            20                  25                  30

Thr Ile Glu Gln Glu Lys Gln Ala Lys
        35                  40

<210> SEQ ID NO 6
<211> LENGTH: 41
<212> TYPE: PRT
<213> ORGANISM: Sus scrofa

<400> SEQUENCE: 6

Ala Asp Lys Pro Asp Met Gly Glu Ile Asn Ser Phe Asp Lys Ala Lys
1               5                   10                  15

Leu Lys Lys Thr Glu Thr Gln Glu Lys Asn Thr Leu Pro Thr Lys Glu
            20                  25                  30

Thr Ile Glu Gln Glu Lys Gln Ala Lys
        35                  40

<210> SEQ ID NO 7
<211> LENGTH: 43
<212> TYPE: PRT
<213> ORGANISM: Homo sapiens

<400> SEQUENCE: 7

```
Ala Asp Lys Pro Asp Met Gly Glu Ile Ala Ser Phe Asp Lys Ala Lys
1               5                   10                  15

Leu Lys Lys Thr Glu Thr Gln Glu Lys Asn Thr Leu Pro Thr Lys Glu
                20                  25                  30

Thr Ile Glu Gln Glu Lys Arg Ser Glu Ile Ser
        35                  40
```

<210> SEQ ID NO 8
<211> LENGTH: 41
<212> TYPE: PRT
<213> ORGANISM: Salmo gairdneri

<400> SEQUENCE: 8

```
Ser Asp Lys Pro Asn Leu Glu Glu Val Ala Ser Phe Asp Lys Thr Lys
1               5                   10                  15

Leu Lys Lys Thr Glu Thr Gln Glu Lys Asn Pro Leu Pro Thr Lys Glu
                20                  25                  30

Thr Ile Glu Gln Glu Lys Gln Ala Ser
        35                  40
```

<210> SEQ ID NO 9
<211> LENGTH: 42
<212> TYPE: PRT
<213> ORGANISM: Salmo gairdneri

<400> SEQUENCE: 9

```
Ser Asp Lys Pro Asp Leu Ala Glu Val Ser Asn Phe Asp Lys Thr Lys
1               5                   10                  15

Leu Lys Lys Thr Glu Thr Gln Glu Lys Asn Pro Leu Pro Thr Lys Glu
                20                  25                  30

Thr Ile Glu Gln Glu Lys Gln Ala Thr Ala
        35                  40
```

<210> SEQ ID NO 10
<211> LENGTH: 43
<212> TYPE: PRT
<213> ORGANISM: Perca fluviatilis

<400> SEQUENCE: 10

```
Ser Asp Lys Pro Asp Ile Ser Glu Val Thr Ser Phe Asp Lys Thr Lys
1               5                   10                  15

Leu Lys Lys Thr Glu Thr Gln Glu Lys Asn Pro Leu Pro Ser Lys Glu
                20                  25                  30

Thr Ile Glu Gln Glu Lys Ala Ala Ala Thr Ser
        35                  40
```

<210> SEQ ID NO 11
<211> LENGTH: 41
<212> TYPE: PRT
<213> ORGANISM: Balaenoptera acutorostrata

<400> SEQUENCE: 11

```
Ala Asp Lys Pro Asp Met Gly Glu Ile Ala Ser Phe Asp Lys Ala Lys
1               5                   10                  15

Leu Lys Lys Thr Glu Thr Gln Glu Lys Asn Thr Leu Pro Thr Lys Glu
                20                  25                  30

Thr Ile Glu Gln Glu Lys Gln Ala Lys
        35                  40
```

<210> SEQ ID NO 12

```
<211> LENGTH: 40
<212> TYPE: PRT
<213> ORGANISM: Arbacia punctulata

<400> SEQUENCE: 12

Ser Asp Lys Pro Asp Ile Ser Glu Val Ser Ser Phe Asp Lys Thr Lys
1               5                   10                  15

Leu Lys Lys Thr Glu Thr Ala Glu Lys Asn Thr Leu Pro Thr Lys Glu
            20                  25                  30

Thr Ile Glu Gln Glu Leu Thr Ala
        35                  40

<210> SEQ ID NO 13
<211> LENGTH: 44
<212> TYPE: PRT
<213> ORGANISM: Homo sapiens

<400> SEQUENCE: 13

Ser Asp Lys Pro Asp Leu Ser Glu Val Glu Thr Phe Asp Lys Ser Lys
1               5                   10                  15

Leu Lys Lys Thr Asn Thr Glu Glu Lys Asn Thr Leu Pro Ser Lys Glu
            20                  25                  30

Thr Ile Gln Gln Glu Lys Glu Tyr Asn Gln Arg Ser
        35                  40

<210> SEQ ID NO 14
<211> LENGTH: 40
<212> TYPE: PRT
<213> ORGANISM: Argopecten irradians

<400> SEQUENCE: 14

Ser Asp Lys Pro Phe Val Ser Glu Val Ala Asn Phe Asp Lys Ser Lys
1               5                   10                  15

Leu Lys Lys Thr Glu Thr Ala Glu Lys Asn Thr Leu Pro Thr Lys Glu
            20                  25                  30

Thr Ile Gln Gln Glu Lys Glu Ala
        35                  40

<210> SEQ ID NO 15
<211> LENGTH: 40
<212> TYPE: PRT
<213> ORGANISM: Arbacia punctulata

<400> SEQUENCE: 15

Ala Asp Lys Pro Asp Val Ser Glu Val Ser Thr Phe Asp Lys Ser Lys
1               5                   10                  15

Leu Lys Lys Thr Glu Thr Gln Glu Lys Asn Thr Leu Pro Thr Lys Asp
            20                  25                  30

Thr Ile Glu Gln Glu Lys Gln Gly
        35                  40
```